United States Patent
Imai et al.

(10) Patent No.: US 12,306,145 B2
(45) Date of Patent: May 20, 2025

(54) INSPECTION APPARATUS

(71) Applicant: SHIMADZU CORPORATION, Kyoto (JP)

(72) Inventors: Akio Imai, Tsukuba (JP); Takayuki Sato, Tsukuba (JP)

(73) Assignee: SHIMADZU CORPORATION, Kyoto (JP)

( * ) Notice: Subject to any disclaimer, the term of this patent is extended or adjusted under 35 U.S.C. 154(b) by 364 days.

(21) Appl. No.: 18/005,501

(22) PCT Filed: Jul. 15, 2021

(86) PCT No.: PCT/JP2021/026574
§ 371 (c)(1),
(2) Date: Jan. 13, 2023

(87) PCT Pub. No.: WO2022/014666
PCT Pub. Date: Jan. 20, 2022

(65) Prior Publication Data
US 2023/0288382 A1 Sep. 14, 2023

(30) Foreign Application Priority Data
Jul. 17, 2020 (JP) .................................. 2020-122726

(51) Int. Cl.
*G01N 33/18* (2006.01)
*B01D 15/34* (2006.01)
(Continued)

(52) U.S. Cl.
CPC ............. *G01N 30/16* (2013.01); *B01D 15/34* (2013.01); *G01N 30/74* (2013.01); *G01N 33/1846* (2013.01); *G01N 2030/027* (2013.01)

(58) Field of Classification Search
CPC ........ G01N 30/04; G01N 30/16; G01N 30/18; G01N 30/20; G01N 30/22; G01N 30/24;
(Continued)

(56) References Cited

U.S. PATENT DOCUMENTS

2017/0209811 A1\* 7/2017 Dlugasch ............ B01D 15/1878
2019/0302085 A1 10/2019 Yano
(Continued)

FOREIGN PATENT DOCUMENTS

| CN | 109425673 A | \* | 3/2019 | ........... B01D 15/305 |
|---|---|---|---|---|
| JP | 2010169691 A | \* | 8/2010 | |
| JP | 2019-178902 A | | 10/2019 | |

OTHER PUBLICATIONS

Nobuyuki Kawasaki et al., "Consideration for molecular weight distribution of DOC in Kasumigaura using size-exclusion chromatography equipped with TOC detector", The Japanese Society of Limnology, the 72nd Meeting, a collection of abstracts of lectures, Sep. 2007, Session ID: 3C05, 2 pages.
(Continued)

*Primary Examiner* — Herbert K Roberts
(74) *Attorney, Agent, or Firm* — Sughrue Mion, PLLC (57) ABSTRACT

An inspection apparatus comprises a first channel that passes an aqueous sample therethrough, a second channel that passes a phosphate eluent therethrough, a separation device that separates by size a group of substances contained in the aqueous sample, and a TOC device that oxidizes each substance separated by the separation device by size and measures organic carbon contained in each substance. The separation device includes a column for size-exclusion chromatography and a sample injection unit that introduces the aqueous sample into a mobile phase passed through the first channel. The second channel is connected to the first channel between the column and the sample injection unit, and
(Continued)

causes the phosphate eluent to merge with the aqueous sample between the sample injection unit and the column.

5 Claims, 4 Drawing Sheets

(51) Int. Cl.
*G01N 30/16* (2006.01)
*G01N 30/74* (2006.01)
*G01N 30/02* (2006.01)

(58) Field of Classification Search
CPC ....... G01N 2030/162; G01N 2030/165; G01N 2030/167; G01N 2030/185; G01N 2030/201; G01N 2030/202; G01N 2030/204; G01N 2030/205; G01N 2030/207; G01N 2030/208; G01N 33/18; G01N 33/1846; B01D 15/34
See application file for complete search history.

(56) References Cited

U.S. PATENT DOCUMENTS

2020/0173968 A1\* 6/2020 Li .................... G01N 21/3504
2021/0349060 A1\* 11/2021 Fogwill ............... G01N 30/468

OTHER PUBLICATIONS

Nobuyuki Kawasaki et al., "Fast and precise method for HPLC-size exclusion chromatography with UV and TOC (NDIR) detection: Importance of multiple detectors to evaluate the characteristics of dissolved organic matter", Water Research, 2011, pp. 6240-6248, vol. 45.
International Search Report for PCT/JP2021/026574 dated Sep. 28, 2021.
Written Opinion for PCT/JP2021/026574 dated Sep. 28, 2021.

\* cited by examiner

INSPECTION APPARATUS

CROSS REFERENCE TO RELATED APPLICATIONS

This application is a National Stage of International Application No. PCT/JP2021/026574 filed Jul. 15, 2021, claiming priority based on Japanese Patent Application No. 2020-122726 filed Jul. 17, 2020.

TECHNICAL FIELD

The present invention relates to an inspection apparatus that inspects an aqueous sample.

BACKGROUND ART

In order to inspect an aqueous sample, an amount of a DOM (a dissolved organic matter) in water is inspected. In order to determine the amount of the DOM, an amount of TOC (total organic carbon) is used as an indicator for the inspection. The amount of TOC is determined by oxidizing an organic matter (organic carbon) to generate carbon dioxide, and measuring the generated carbon dioxide with an NDIR (nondispersive infrared) sensor or the like.

As methods of oxidizing organic carbon are known a method using a catalyst to combust it, a method using ultraviolet light, a two-step oxidation method, etc. (PTL 1).

Researches in recent years have revealed that decomposability varies depending on the DOM's molecular size. NPL 1 discloses an inspection apparatus comprising SEC (size-exclusion chromatography) and a TOC detector combined together to determine a molecular weight distribution of a DOM.

CITATION LIST

Patent Literature

PTL 1: Japanese Patent Laying-Open No. 2019-178902

Non Patent Literature

NPL 1: Nobuyuki KAWASAKI, Kazuo MATSUSHIGE, Akio IMAI, Kazuhiro KOMATSU, Fumikazu OGISHI, Masato YAHATA, Hirohisa MIKAMI, and Takeshi GOTO, "Consideration for molecular weight distribution of DOC in Kasumigaura using size-exclusion chromatography equipped with TOC detector," The Japanese Society of Limnology, the 72nd Meeting, a collection of abstracts of lectures, Session ID: 3C5, September 2007

SUMMARY OF INVENTION

Technical Problem

The inspection apparatus disclosed in NPL 1 that combines a SEC and a TOC detector can also detect organic carbon, which cannot be detected with an ultraviolet-visible spectrophotometer, a fluorometer, or the like.

The inspection apparatus disclosed in NPL 1 uses a SEC to determine a molecular weight distribution of a DOM, and introducing an aqueous sample into the SEC requires introducing the aqueous sample into a mobile phase having had an eluent added thereto. The eluent and the aqueous sample are significantly different in ionic strength, and accordingly, the ionic strength of the aqueous sample is adjusted in advance so as to be equivalent to the ionic strength of the eluent.

However, when the ionic strength of the aqueous sample is adjusted in advance, a problem arises in that the aqueous sample's polymer concentration decreases as time elapses. Further, there is also a problem in that as the aqueous sample's polymer concentration decreases with time the apparatus cannot adopt an autosampler or a similar configuration for which there is a long period of time between setting the aqueous sample and conducting measurement.

The present invention has been made to address such an issue and an object of the present invention is to provide an apparatus that does not require previously adjusting an aqueous sample in ionic strength.

Solution to Problem

An inspection apparatus according to an aspect of the present invention is an inspection apparatus that inspects an aqueous sample. The inspection apparatus comprises a first channel that passes an aqueous sample therethrough, a second channel that passes a phosphate eluent therethrough, a separation device that separates by size a group of substances contained in the aqueous sample, and a measurement unit that oxidizes each substance separated by the separation device by size and measures organic carbon contained in each substance. The separation device includes a column for size-exclusion chromatography and an introduction unit that introduces the aqueous sample into a mobile phase passed through the first channel. The second channel is connected to the first channel between the column and the introduction unit, and causes the phosphate eluent to merge with the aqueous sample between the introduction unit and the column.

Advantageous Effects of Invention

The present inspection apparatus has a second channel connected between a column and an introduction unit and causes a phosphate eluent to merge with an aqueous sample between the introduction unit and the column, and the present inspection apparatus thus does not require previously adjusting the aqueous sample in ionic strength, and can suppress variation in polymer concentration of the aqueous sample and accurately measure organic carbon contained in each substance.

DESCRIPTION OF EMBODIMENTS

Hereinafter, an embodiment of the present invention will be described in detail with reference to the accompanying drawings. In the figures, identical or corresponding components are identically denoted and will not be described repeatedly.

[Configuration of Inspection Apparatus 1]

Figure 1:
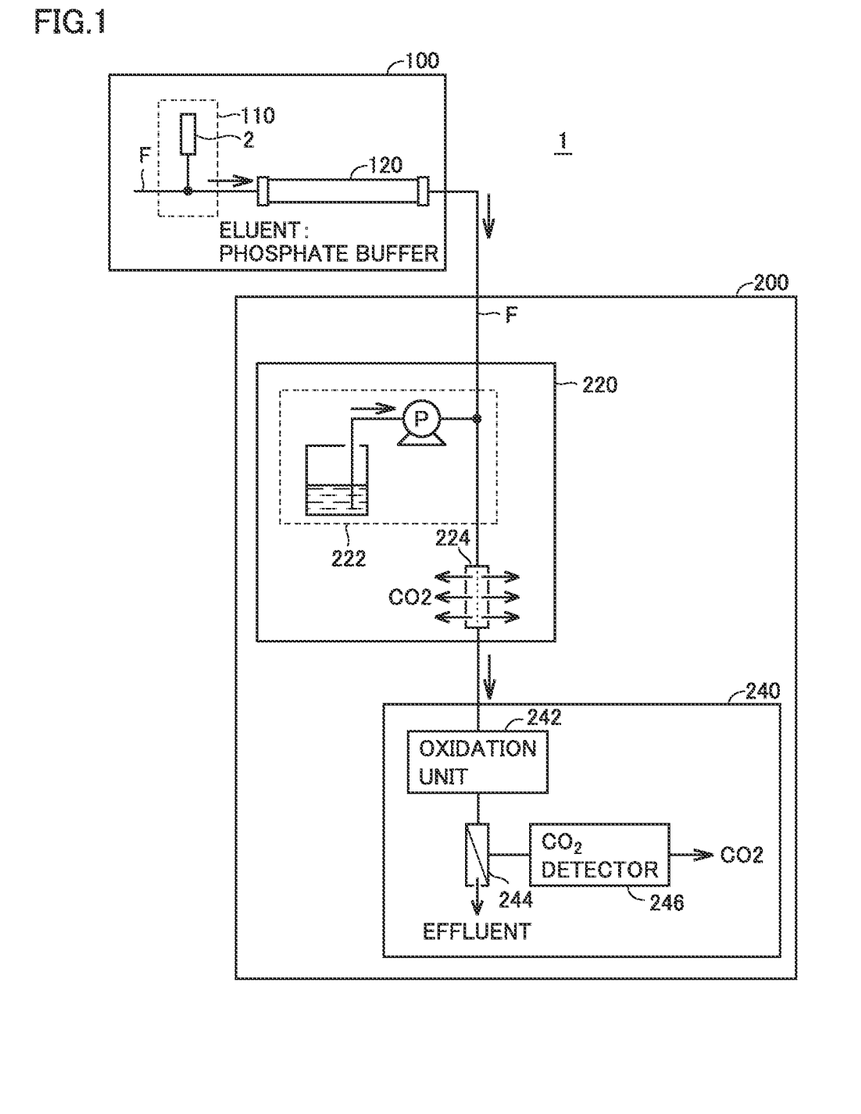
FIG. 1 is a diagram schematically showing a configuration of an inspection apparatus 1 according to an embodiment.

FIG. 1 is a diagram schematically showing a configuration of an inspection apparatus 1 according to an embodiment. Inspection apparatus 1 is an apparatus that inspects an aqueous sample 2. Referring to FIG. 1, inspection apparatus 1 comprises a separation device 100 and a TOC device 200 (or a measurement unit). Inspection apparatus 1 separates a substance in aqueous sample 2 by separation device 100 by size, oxidizes each substance eluted from separation device 100 in an order depending on size, and measures by TOC device 200 an amount of organic carbon (or an amount of TOC) contained in each substance. Thus, inspection apparatus 1 measures an amount of TOC for each organic matter dissolved in aqueous sample 2 having a different size.

Separation device 100 separates by size a group of substances contained in aqueous sample 2 to be measured. Separation device 100 typically employs SEC to separate by size the group of substances contained in aqueous sample 2. Separation device 100 includes a sample injection unit 110 (or an introduction unit) and a column 120.

Sample injection unit 110 injects aqueous sample 2 into a channel F that passes an eluent therethrough. Typically, a phosphate buffer can be used as the eluent. The eluent used is selected in view of the type of column 120 and an impact on TOC device 200 and TOC measurement.

Substances in aqueous sample 2 injected into channel F from sample injection unit 110 are separated by molecular size as the substances pass through column 120. More specifically, substances having larger molecular sizes (typically having larger molecular weights) are sequentially eluted from column 120 and sent to TOC device 200.

TOC device 200 measures an amount of TOC contained in an eluate (i.e., a mixture of a separated substance and the eluent) received from column 120. TOC device 200 includes a pretreatment unit 220 that removes inorganic carbon contained in the separated substance, and a measurement unit 240 that measures a total amount of carbon (i.e., an amount of TOC) contained in the substance after inorganic carbon is removed.

Pretreatment unit 220 receives an eluate from column 120 and acidifies the received eluate to convert inorganic carbon in aqueous sample 2 into carbon dioxide and thus remove it. Pretreatment unit 220 includes an addition unit 222 that adds into a channel a reagent that acidifies the eluate, and a degassing unit 224 that degasses carbon dioxide.

Addition unit 222 is provided at an inlet of TOC device 200. The reagent added by addition unit 222 is, for example, phosphoric acid, sulfuric acid, or the like. Addition unit 222 delivers the reagent to channel F by a pump P.

Degassing unit 224 is provided downstream of addition unit 222. Degassing unit 224 is typically a degasser, and degasses carbon dioxide derived from inorganic carbon generated by adding the reagent in addition unit 222. The eluate degassed in degassing unit 224 (a mixture of aqueous sample 2 and the eluent) is delivered to measurement unit 240.

Measurement unit 240 oxidizes organic carbon in aqueous sample 2 having had inorganic carbon removed therefrom into carbon dioxide, and measures the generated carbon dioxide to measure an amount of TOC.

Measurement unit 240 includes an oxidation unit 242 that oxidizes organic carbon in aqueous sample 2 having had inorganic carbon removed therefrom, a gas-liquid separation unit 244 that separates carbon dioxide (or gas) generated by oxidizing organic carbon from a liquid, and a $CO_2$ detector 246 that measures the separated and thus obtained carbon dioxide.

Oxidation unit 242 oxidizes organic carbon by a wet UV oxidation method. More specifically, oxidation unit 242 adds an oxidizing agent to aqueous sample 2 having had inorganic carbon removed therefrom (or an eluate) and subsequently exposes it to ultraviolet light to oxidize organic carbon. A configuration of oxidation unit 242 will be described later with reference to FIG. 2. When the amount of TOC is lower than a predetermined amount, oxidation unit 242 may not add the oxidizing agent.

Gas-liquid separation unit 244 separates liquid from gas, and externally discharges the liquid as effluent and delivers the gas to $CO_2$ detector 246. The gas separated by gas-liquid separation unit 244 at least includes carbon dioxide generated by oxidizing organic carbon.

$CO_2$ detector 246 measures the concentration of the carbon dioxide in the gas delivered from gas-liquid separation unit 244. $CO_2$ detector 246 is typically a nondispersive infrared gas detector (a NDIR detector). $CO_2$ detector 246 is not limited to the NDIR detector, and may be any other detector that can measure carbon dioxide concentration.

[Configuration of Separation Device 100 and Pretreatment Unit 220]

Figure 2:
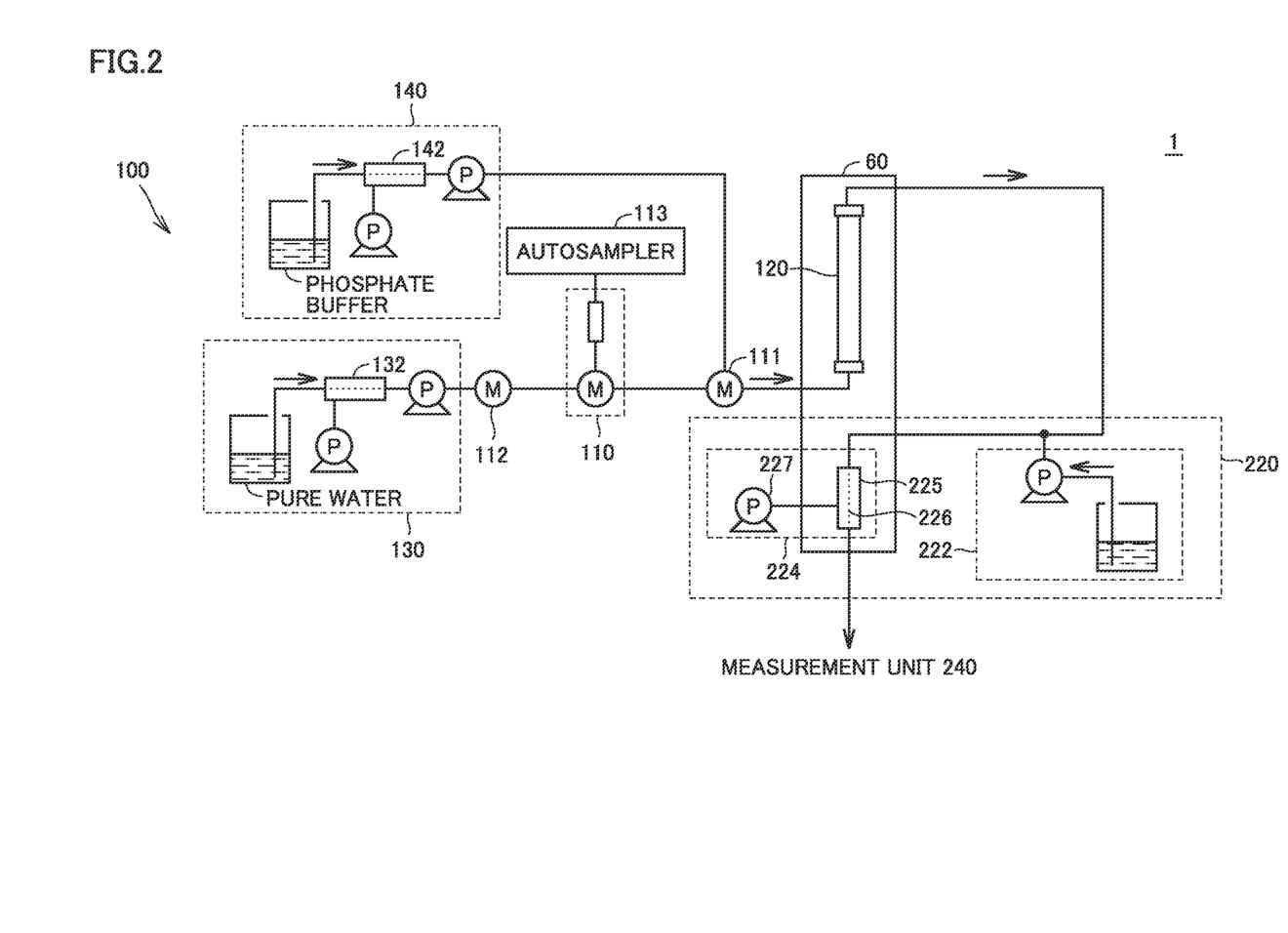
FIG. 2 is a diagram schematically showing a configuration of a separation device 100 and a pretreatment unit 220.

FIG. 2 is a diagram schematically showing a configuration of separation device 100 and pretreatment unit 220. In the present embodiment, an eluent is produced by delivering pure water and a phosphate buffer solution by separate pumps and mixing them in channel F.

Separation device 100 includes a first solvent delivery unit 130 that delivers water and a second solvent delivery unit 140 that delivers a phosphate buffer (a phosphate eluent). The water delivered from first solvent delivery unit 130 to column 120 flows as a mobile phase to column 120. Sample injection unit 110 is provided on a channel extending from first solvent delivery unit 130 to column 120 (a first channel), and aqueous sample 2 injected by sample injection unit 110 is passed to column 120 by the water delivered from first solvent delivery unit 130.

Second solvent delivery unit 140 is connected to a channel that extends from first solvent delivery unit 130 to column 120 (the first channel) via a channel that passes the phosphate buffer (a second channel). The channel from first solvent delivery unit 130 to column 120 (the first channel) includes a peak mixer 111 provided downstream of sample injection unit 110 (a first mixer), and an LC mixer 112 provided upstream of sample injection unit 110 (a second mixer). Second solvent delivery unit 140 is connected at peak mixer 111, rather than LC mixer 112, and causes the phosphate buffer to merge with the water having had aqueous sample 2 injected thereinto by sample injection unit 110 (a solvent, a mobile phase).

Second solvent delivery unit 140 can also connect at LC mixer 112 and cause the phosphate buffer to merge with water before aqueous sample 2 is injected thereinto. However, when the phosphate buffer is merged with water before aqueous sample 2 is injected thereinto, it is necessary to previously adjust the aqueous sample in ionic strength to be equivalent to that of the eluent as the phosphate buffer and the aqueous sample are significantly different in ionic strength.

However, when phosphoric acid is added to previously adjust aqueous sample 2 in ionic strength, aqueous sample 2 decreases in polymer concentration with time. It is believed that decrease in polymer concentration of aqueous sample 2 is caused by precipitation of polymer of aqueous sample 2 by addition of phosphoric acid to adjust ionic strength. Further, as aqueous sample 2 decreases in polymer concentration with time, an autosampler or a similar configuration in which there is a long period of time between setting aqueous sample 2 and conducting measurement cannot be adopted.

Accordingly, in inspection apparatus 1 according to the present embodiment, second solvent delivery unit 140 is connected to peak mixer 111, rather than LC mixer 112, and a phosphate buffer is caused to merge with water having had aqueous sample 2 injected thereinto by sample injection unit 110. That is, in inspection apparatus 1, the phosphate buffer is merged with aqueous sample 2 while it reaches from sample injection unit 110 to column 120. Here, aqueous sample 2 while it reaches from sample injection unit 110 to column 120 may be that at any location along a channel reaching from sample injection unit 110 to column 120. Inspection apparatus 1 that causes a phosphate buffer to merge with aqueous sample 2 while it reaches from sample injection unit 110 to column 120 does not require previously adjusting aqueous sample 2 in ionic strength, and can suppress variation in polymer concentration of aqueous sample 2 and accurately measure an amount of TOC. In inspection apparatus 1, an autosampler 113 is connected to sample injection unit 110. Thus, inspection apparatus 1 allows a plurality of aqueous samples 2 to be set and can automatically measure an amount of TOC for each aqueous sample 2. As a matter of course, inspection apparatus 1 may not have autosampler 113 connected to sample injection unit 110, and may instead allow each aqueous sample 2 to be injected from sample injection unit 110.

First solvent delivery unit 130 and second solvent delivery unit 140 include a first degassing unit 132 and a second degassing unit 142, respectively, as a pretreatment unit that degasses gas dissolved in a solvent.

Degassing unit 224 that removes carbon dioxide derived from inorganic carbon includes a container 225, a tube 226 disposed in container 225, and a vacuum pump 227 that decreases pressure in container 225.

Tube 226 is connected to channel F passing aqueous sample 2 therethrough. Tube 226 is a gas permeable tube, and is made of a material allowing gas to permeate therethrough while preventing liquid from permeating therethrough. Tube 226 is typically, but not limited to, a gas permeable tube made of amorphous Teflon® resin material, a hollow fiber membrane made of polytetrafluoroethylene, or the like.

When vacuum pump 227 is operated to vacuum container 225, gas in channel F moves to outside of tube 226, and carbon dioxide derived from inorganic carbon is removed from aqueous sample 2. When container 225 having tube 226 disposed therein can be kept high in temperature, carbon dioxide can be degassed more efficiently. Accordingly, it is desirable to provide a temperature maintaining unit to maintain the temperature of container 225.

Inspection apparatus 1 further comprises a column oven 60. Column oven 60 controls column 120 in temperature. Further, container 225 of degassing unit 224 that removes carbon dioxide derived from inorganic carbon is disposed in column oven 60. That is, column oven 60 controls column 120 and container 225 in temperature. In other words, column oven 60 not only controls column 120 in temperature but also serves as a temperature maintaining unit to maintain the temperature of container 225.

While the example shown in FIG. 2 shows an example in which column 120 and container 225 are controlled in temperature by column oven 60, any other device that can maintain temperature of column 120 and container 225 may instead be used.

[Configuration of Oxidation Unit 242]

Figure 3:
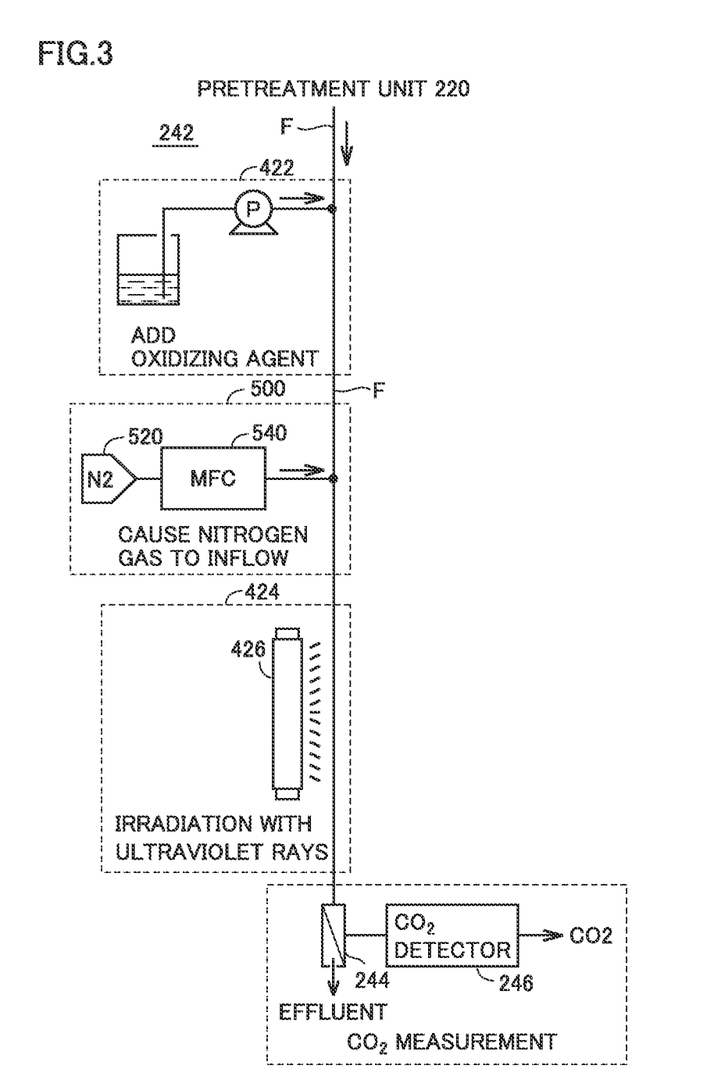
FIG. 3 is a diagram schematically showing a configuration of an oxidation unit.

FIG. 3 is a diagram schematically showing a configuration of oxidation unit 242. Oxidation unit 242 includes an addition unit 422 and an irradiation unit 424. Addition unit 422 is provided at an inlet of oxidation unit 242. Irradiation unit 424 is provided downstream of addition unit 422.

Addition unit 422 adds an oxidizing agent to aqueous sample 2 having had inorganic carbon removed therefrom (or an eluate). The oxidizing agent is for example sodium persulfate. Addition unit 422 delivers the oxidizing agent to channel F by pump P.

Irradiation unit 424 includes a UV lamp 426 that irradiates aqueous sample 2 (or an eluate) passing through channel F with ultraviolet rays. Irradiation unit 424 includes a cylindrical UV lamp and a helical channel receiving ultraviolet rays from the UV lamp.

An inflow unit 500 is provided along channel F between addition unit 422 and irradiation unit 424. Inflow unit 500 causes a carbon-free gas to flow into channel F while controlling the gas in flow rate. The carbon-free gas is for example nitrogen, helium, oxygen, etc. In this embodiment, the carbon-free gas is nitrogen.

Inflow unit 500 includes a nitrogen source 520 and a mass flow controller 540. Nitrogen gas is supplied from nitrogen source 520 to channel F. Mass flow controller 540 controls nitrogen gas supplied to channel F in flow rate.

More specifically, mass flow controller 540 controls nitrogen gas in flow rate so that the nitrogen gas is supplied from nitrogen source 520 to channel F at a fixed flow rate.

[Inspection Apparatus 1a According to a Modified Example]

Figure 4:
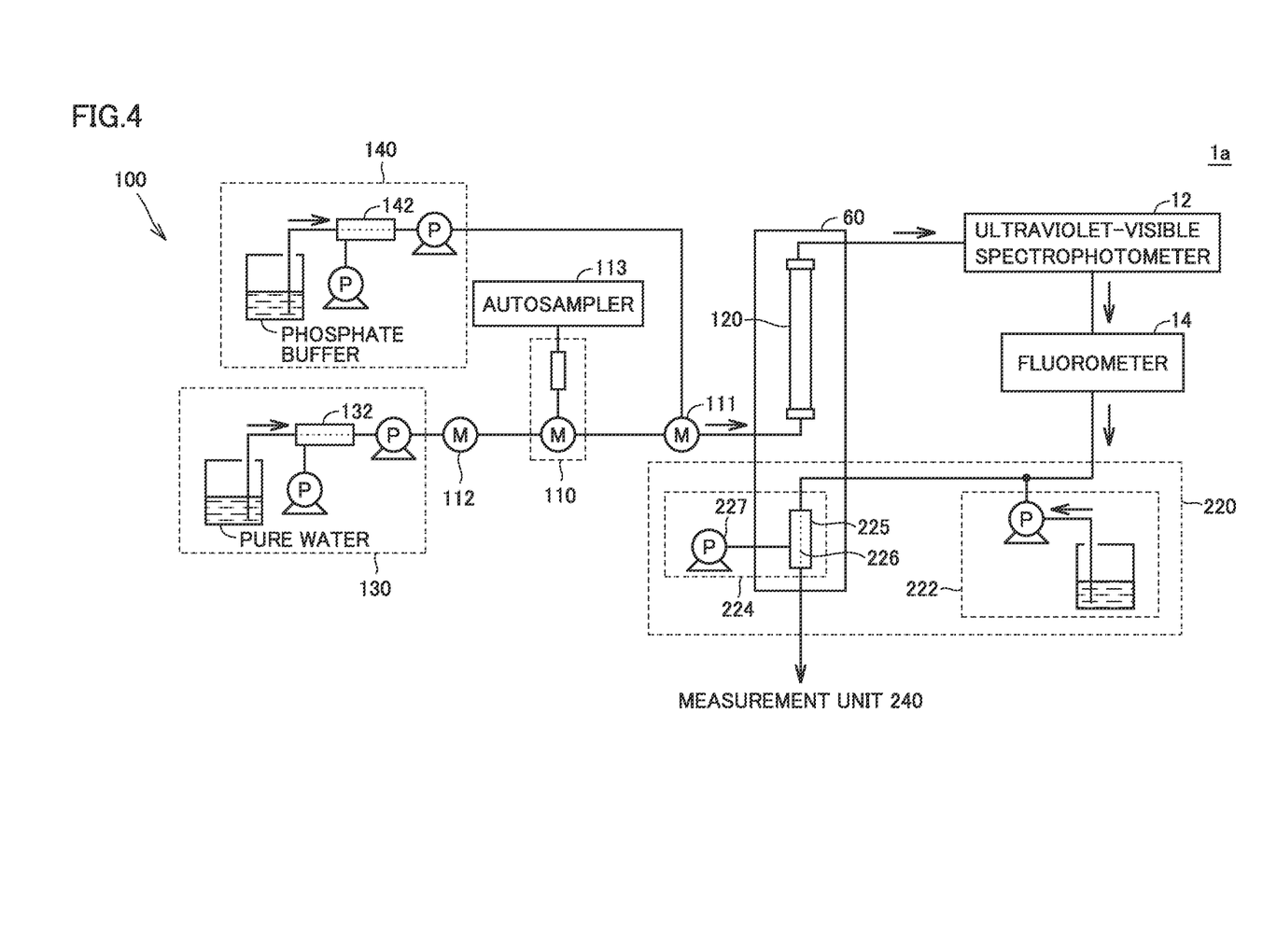
FIG. 4 is a diagram schematically showing a configuration of an inspection apparatus 1a according to a modified example.

FIG. 4 is a diagram schematically showing a configuration of an inspection apparatus 1a according to a modified example. In the above embodiment, inspection apparatus 1 comprises TOC device 200 alone as a measurement device. Inspection apparatus 1 may comprise another measurement device in addition to TOC device 200. Inspection apparatus 1a according to the modified example differs from inspection apparatus 1 indicated in the above embodiment in that inspection apparatus 1a further comprises an ultraviolet-visible spectrophotometer 12 and a fluorometer 14 in addition to TOC device 200.

Ultraviolet-visible spectrophotometer 12 and fluorometer 14 are provided along channel F between separation device 100 and TOC device 200. More specifically, ultraviolet-visible spectrophotometer 12 and fluorometer 14 are provided on a route between column 120 and addition unit 222.

TOC device 200 subjects an aqueous sample to chemical treatment and thus measures carbon dioxide derived from organic carbon to measure an amount of TOC. In contrast, ultraviolet-visible spectrophotometer 12 and fluorometer 14 do not subject the aqueous sample to physical or chemical treatment and can thus measure the aqueous sample without changing a substance in composition, shape or function.

Accordingly, by disposing ultraviolet-visible spectrophotometer 12, fluorometer 14, and TOC device 200 in this order, each measurement device can be disposed on a single channel, and it is not necessary to branch an eluate that is eluted from separation device 100 into each measurement device. This can eliminate the necessity of reducing an amount of liquid of the aqueous sample used in each measurement device, and thus maintain measurement accuracy.

Inspection apparatus 1a according to the modified example comprises ultraviolet-visible spectrophotometer 12 and fluorometer 14. The inspection apparatus may comprise one of ultraviolet-visible spectrophotometer 12 and fluorometer 14 in addition to TOC device 200.

[Aspects]

It is understood by those skilled in the art that the above-described exemplary embodiments are specific examples of the following aspects:

(Clause 1) An inspection apparatus (1, 1a) according to one aspect is an inspection apparatus that inspects an aqueous sample (2), and comprises: a first channel that passes an aqueous sample therethrough; a second channel that passes a phosphate eluent therethrough; a separation device (100) that separates by size a group of substances contained in the aqueous sample; and a measurement unit (200) that oxidizes each substance separated by size by the separation device and measures organic carbon contained in each substance, the separation device including a column (120) for size-exclusion chromatography, and an introduction unit (110) that introduces the aqueous sample into a mobile phase passed through the first channel, the second channel being connected to the first channel between the column and the introduction unit, and causing the phosphate eluent to merge with the aqueous sample between the introduction unit and the column.

The inspection apparatus according to clause 1 has a second channel connected between a column and an introduction unit and causes a phosphate eluent to merge with an aqueous sample between the introduction unit and the column, and the present inspection apparatus thus does not require previously adjusting the aqueous sample in ionic strength, and can suppress variation in polymer concentration of the aqueous sample and accurately measure an amount of TOC.

(Clause 2) In the inspection apparatus according to clause 1, the separation device further includes a first mixer (111) that is provided downstream of the introduction unit and mixes a solvent with the mobile phase, the second channel is connected to the first mixer, and the first mixer receives the phosphate eluent from the second channel and mixes the received phosphate eluent with the mobile phase having had the aqueous sample introduced therein.

The inspection apparatus according to clause 2 can mix the phosphate eluent received from the second channel with the mobile phase having had the aqueous sample introduced therein by the first mixer, and thus suppress variation in polymer concentration of the aqueous sample and accurately measure an amount of TOC.

(Clause 3) In the inspection apparatus according to clause 2, the separation device further includes a second mixer (112) that is provided upstream of the introduction unit and mixes the solvent with the mobile phase.

The inspection apparatus according to clause 3 can mix the solvent with the mobile phase before the second mixer introduces the aqueous sample into the mobile phase.

(Clause 4) In the inspection apparatus according to any one of clauses 1 to 3, the aqueous sample introduced at the introduction unit is supplied from an autosampler (113).

The inspection apparatus according to clause 4 allows a plurality of aqueous samples to be set and can measure an amount of TOC of each aqueous sample automatically.

(Clause 5) The inspection apparatus according to any one of clauses 1 to 4 further comprises at least one of an ultraviolet-visible spectrophotometer (12) and a spectrofluorometer (14) at a channel between the separation device and the TOC device.

The inspection apparatus according to clause 5 can perform measurement at each measurement device without branching to each measurement device the aqueous sample eluted from the column. As there is no need to branch to each measurement device the aqueous sample eluted from the column, an amount of liquid of the aqueous sample that is used in each measurement device can be maintained, and as a result, measurement accuracy can be maintained.

It should be understood that the presently disclosed embodiments are illustrative and non-restrictive in any respect. The scope of the present invention is defined by the terms of the claims, rather than the above description of the embodiments, and is intended to include any modifications within the meaning and scope equivalent to the terms of the claims.

REFERENCE SIGNS LIST 1, 1a inspection apparatus, 2 aqueous sample, 12 ultraviolet-visible spectrophotometer, 14 fluorometer, 60 column oven, 100 separation device, 110 sample injection unit, 120 column, 130 first solvent delivery unit, 132 first degassing unit, 140 second solvent delivery unit, 142 second degassing unit, 200 TOC device, 220 pretreatment unit, 222 addition unit, 224 degassing unit, 225 container, 226 tube, 227 vacuum pump, 240 measurement unit, 242 oxidation unit, 244 gas-liquid separation unit, 246 $CO_2$ detector, F channel, M mixer, P pump.

The invention claimed is:

1. An inspection apparatus that inspects an aqueous sample, comprising:
   a first channel that passes the aqueous sample therethrough;
   a second channel that passes a phosphate eluent therethrough;
   a separation device that separates by size a group of substances contained in the aqueous sample; and
   a measurement unit that oxidizes each substance separated by size by the separation device and measures organic carbon contained in each substance,
   the separation device including
      a column for size-exclusion chromatography, and
      an introduction unit that introduces the aqueous sample into a mobile phase passed through the first channel,
   the second channel being connected to the first channel between the column and the introduction unit, and causing the phosphate eluent to merge with the aqueous sample between the introduction unit and the column.

2. The inspection apparatus according to claim 1, wherein the separation device further includes a first mixer that is provided downstream of the introduction unit and mixes a solvent with the mobile phase,
   the second channel is connected to the first mixer, and
   the first mixer receives the phosphate eluent from the second channel and mixes the received phosphate eluent with the mobile phase having had the aqueous sample introduced therein.

3. The inspection apparatus according to claim 2, wherein the separation device further includes a second mixer that is provided upstream of the introduction unit and mixes the solvent with the mobile phase.

4. The inspection apparatus according to claim 1, wherein the aqueous sample introduced at the introduction unit is supplied from an autosampler.

5. The inspection apparatus according to claim 1, further comprising at least one of an ultraviolet-visible spectrophotometer and a spectrofluorometer at a channel between the separation device and the measurement unit.

\* \* \* \* \*